United States Patent [19]

Poncioni

[11] 4,250,315
[45] Feb. 10, 1981

[54] LIGHT-SCREENING BENZOXAZOLE DERIVATIVES

[75] Inventor: Bruno Poncioni, Muttenz, Switzerland

[73] Assignee: Hoffmann-La Roche Inc., Nutley, N.J.

[21] Appl. No.: 86,253

[22] Filed: Oct. 18, 1979

[30] Foreign Application Priority Data

Oct. 31, 1978 [CH] Switzerland ............... 11210/78
Aug. 27, 1979 [CH] Switzerland ............... 7758/79

[51] Int. Cl.³ .............................................. C07D 263/54
[52] U.S. Cl. .................................. 346/198; 548/217
[58] Field of Search ..................... 548/217; 546/198

[56] References Cited

U.S. PATENT DOCUMENTS

| 2,715,032 | 8/1955 | Sartori | 548/257 |
| 2,793,192 | 5/1957 | Leavitt | 548/217 |
| 3,452,036 | 6/1969 | Crocker et al. | 548/217 |
| 3,551,443 | 12/1970 | Duennevberger | 548/217 |
| 3,585,208 | 6/1971 | Rash et al. | 548/217 |
| 3,586,670 | 6/1971 | Brenneisen et al. | 548/217 |
| 3,696,193 | 10/1972 | Guglielmetti et al. | 548/217 |

FOREIGN PATENT DOCUMENTS 1282855 11/1968 Fed. Rep. of Germany ........... 548/306

OTHER PUBLICATIONS

Hein et al., "J. Am. Chem. Soci.," vol. 79, (1957), pp. 427–429.

Primary Examiner—Anton H. Sutto
Attorney, Agent, or Firm—Jon S. Saxe; Bernard S. Leon; James H. Callwood

[57] ABSTRACT

Benzoxazole derivatives represented by the formula

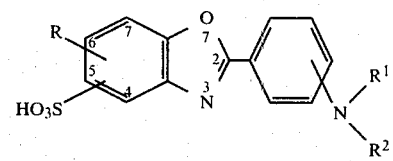

wherein R is in the 5- or 6-position and is hydrogen or an alkyl group containing 1 to 4 carbon atoms and $R^1$ and $R^2$ are independently hydrogen, an alkyl group containing 1 to 4 carbon atoms or a group having the formula—$(XO)_n$—H, wherein X is ethylene or ethylene substituted by methyl or ethyl and which contains a total of 2 to 4 carbon atoms and n is an integer of 1 to 10, at least one of $R^1$ and $R^2$ being other than hydrogen, or $R^1$ and $R^2$, taken together with the nitrogen to which they are attached, form a 5- to 7-membered, saturated heterocyclic ring, and cosmetically acceptable salts thereof. The subject compounds, in combination with a suitable cosmetic carrier, are useful as radiation absorbers, i.e., UV-A filters.

8 Claims, No Drawings

LIGHT-SCREENING BENZOXAZOLE DERIVATIVES

DETAILED DESCRIPTION OF THE INVENTION

The present invention is directed to benzoxazole derivatives represented by the formula

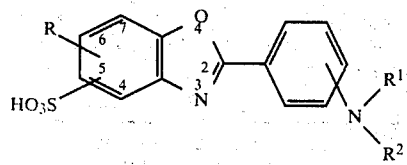 I wherein R is in the 5- or 6-position and is hydrogen or an alkyl group containing 1 to 4 carbon atoms and $R^1$ and $R^2$ are independently hydrogen, an alkyl group containing 1 to 4 carbon atoms or a group having the formula $—(XO)_n—H$, wherein X is ethylene or ethylene substituted by methyl or ethyl and which contains a total of 2 to 4 carbon atoms and n is an integer of 1 to 10, at least one of $R^1$ and $R^2$ being other than hydrogen, or $R^1$ and $R^2$ taken together with the nitrogen to which they are attached, form a 5- to 7-membered, saturated hetrocyclic ring, and cosmetically acceptable salts thereof. The compounds of formula I are useful as absorbers of radiation, i.e., as UV-A absorbers.

The term "alkyl" in formula I includes both straight- and branched-chain alkyl groups containing 1 to 4 carbon atoms., i.e., methyl, ethyl, n-propyl, isopropyl, n-butyl, isobutyl, sec. butyl, and tert. butyl. The term "ethylene substituted by methyl or ethyl" preferably relates to groups represented by the formulae:

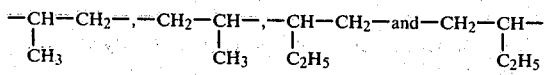

When several symbols X are present, then they are independent of one another.

When $R^1$ and $R^2$ together with the nitrogen to which they are attached form a 5- to 7-membered heterocyclic ring, such rings may contain an additional hetero atom, preferably oxygen, nitrogen or sulfur. Examples of suitable hetero rings in accordance with the present invention include piperidino, pyrrolidino, morpholino, piperazino, and thiomorpholino. Particularly preferred hetero rings are piperidino, pyrrolidino, morpholino and thiomorpholino.

Cosmetically acceptable salts of the compounds of formula I are those obtained by neutralization with a suitable organic or inorganic base, such as, for example, alkali metal salts such as the sodium and potassium salts, the ammonium salts, and the monoethanolamine, diethanolamine, and triethanolamine salts. The triethanolamine salts are particularly preferred.

When R in formula I is alkyl, it is preferably methyl. In formula I, R, $R^1$ and $R^2$, independently, are preferably hydrogen, methyl and methyl, respectfully.

Compounds of formula I having the $HO_3S—$ group in the 5- or 6-position, particularly the 5-position, are preferred embodiments of the present invention. Likewise preferred are compounds of formula I wherein the $—NR^1R^2$ group is in the para position. Particularly preferred are compounds of formula I having the $HO_3S—$ group in the 5-position and the $—NR^1R^2$ group in the para position, and cosmetically acceptable salts thereof. Particularly preferred is 2-(p-dimethylaminophenyl)-benzoxazole-5-sulfonic acid and cosmetically acceptable salts thereof.

A preferred group of compounds in accordance with the present invention are compounds of formula I wherein R is hydrogen and n in the formula $—(XO)_nH$ is 1, i.e., the group XOH wherein X is as previously defined.

In accordance with the present invention, the compounds of formula I may be prepared:

(a) by reacting a sulfonic acid represented by the general formula

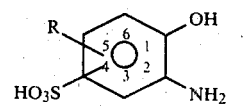 II wherein R is in the 4- or 5-position and is hydrogen or an alkyl group containing 1 to 4 carbon atoms, with a benzoic acid represented by the general formula

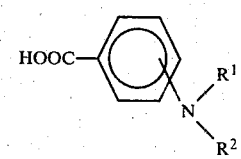 III wherein $R^1$ is hydrogen or an alkyl group containing 1 to 4 carbon atoms and $R^2$ is an alkyl group containing 1 to 4 carbon atoms, or $R^1$ and $R^2$ taken together with the nitrogen to which they are attached, form a 5- to 7-membered, saturated heterocyclic ring, or a reactive derivative thereof, in the presence of a condensing agent; or (b) by reacting a compound of formula I wherein at least one of the symbols $R^1$ and $R^2$ is a hydrogen atom and the other, when not hydrogen, is an alkyl group, or a salt of such a compound, with an alkylene oxide or a mixture of alkylene oxides containing 2 to 4 carbon atoms; or (c) treating a compound represented by the general formula

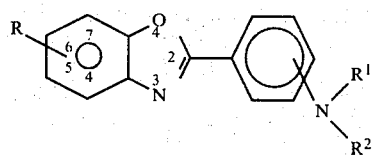 IV wherein R is in the 5- or 6-position and is hydrogen or an alkyl group containing 1 to 4 carbon atoms and $R^1$ and $R^2$ are as defined above in the definition of formula I, with a sulfonating agent, and, if desired, converting the resulting compound of formula I into a salt with a suitable base.

According to embodiment (a) of the process, compounds of formula I are prepared, for example, by condensing 1 equivalent of a sulfonic acid of formula II with 1 equivalent of a benzoic acid of formula III, or a reactive derivative thereof, in the presence of a condensation agent, such as, for example, polyphosphoric acid. The reaction is preferably carried out at a temperature between about 120° C. and about 180° C. The reaction can, however, also be carried out according to one of the other variations of this procedure known from the literature, such as are described, for example, in the article by D. W. Hein, et al., J.A.C.S. 79, p. 427 (1967). Thus, for example, a compound of formula I can be prepared by reacting a sulfonic acid of formula II above with a reactive derivative of a benzoic acid of formula III, such as an ester, the amide, the chloride, or the nitrile.

The reaction between a compound of formula I in which at least one of the symbols $R^1$ and $R^2$ is a hydrogen atom and the other, when not a hydrogen atom, is an alkyl group, or a salt of such a compound, and an alkylene oxide, such as, for example, ethylene oxide, propylene oxide, or butylene oxide, or a mixture of several alkylene oxides according to embodiment (b) above is conventiently carried out using a molar ratio of a compound of formula I to said alkylene oxide or oxides of at least 1:1 to 1:10, when the compound of formula I contains a monoalkylamino group, or of at least 1:1 to 1:20, when the compound of formula I contains an unsubstituted amino group. The reaction is preferably carried out in the absence of a solvent and at a temperature between about 60° C. and about 120° C. The reaction generally lasts from 2 to 6 hours depending on the temperature range and starting materials utilized.

According to embodiment (c) above, a compound of formula IV is treated with a sulfonating agent, such as, for example, oleum or chlorosulfonic acid. This treatment is conveniently carried out in the absence of a solvent and in a temperature range from about 100° C. to about 160° C.

The cosmetically acceptable salts of the comounds of formula I are prepared by neutralizing a compound of formula I with a suitable base such as mentioned above. Suitable bases include, for example, sodium hydroxide, potassium hydroxide, ammonia, monoethanolamine, diethanolamine, triethanolamine, and the like.

The products of the above-described processes can be isolated and purified according to methods conventional in the art.

The starting materials of formulae II and III are either known or can be prepared according to methods conventional in the art from known materials.

The compounds of formula I wherein each of $R^1$ and $R^2$ are hydrogen and the compounds of formula IV, which are used as starting materials in embodiments (b) and (c) above can be prepared in an analogous manner to embodiment (a) as described above.

It is recognized that skin exposed to sunlight undergoes alterations. For years, dermatologists have warned against the deleterious effects of the sun or skin. Such undesirable effects are ascribed to radiation of the wavelength 320 to 400 nm. Heretofore, filters utilized in cosmetic preparations to protect against radiation in this critical wavelength either have insufficient screening capability to because of being insoluble or poorly soluble in water, cannot be incorporated in fat-free and alcohol-free cosmetics.

The benzoxazole derivatives provided by the present invention possess excellent filtering capability in the wavelength range of 320 to 390 nm as is evident from the following Table. Further, the derivatives, especially the salts, are sufficiently water-soluble, thereby facilitating their incorporation in fat-free and alcohol-free cosmetic formulations.

Comparison of the light absorption of a compound of formula I with a known filter in the UV-A range In the following Table the percentage absorption of UV-light in the range 320–400 nm of a 1 mg-% aqueous solution of 2-(p-dimethylaminophenyl)-benzoxazole-5-sulfonic acid is compared with a 1 mg-% aqueous solution of the known UV-A filter 2-hydroxy-4-methoxybenzophenone-5-sulfonic acid, the layer thickness of both solutions being 1 cm.

TABLE

| | Proportion of light absorbed by | |
|---|---|---|
| UV-light wavelength nm | 2-(p-Dimethylaminophenyl)-benzoxazole-5-sulfonic acid % | 2-Hydroxy-4-methoxybenzophenone-5-sulfonic acid % |
| 320 | 81 | 47 |
| 330 | 90 | 43 |
| 340 | 94 | 32 |
| 350 | 94 | 17 |
| 360 | 92 | 7 |
| 370 | 85 | 3 |
| 380 | 57 | 1 |
| 390 | 20 | 0 |
| 400 | 0 | 0 |

From the absorption values it is evident that 2-(p-dimethylaminophenyl)-benzoxazole-5-sulfonic acid absorbs stronger between 320 to 400 nm than the comparison substance. It is also seen that, near the visible light range, i.e. 360–400 nm, 2-(p-dimethylaminophenyl)-benzoxazole-5-sulfonic acid still possesses strong absorption, whereas the comparison substance on longer shows absorption.

The benzoxazole derivatives provided by the present invention also possess the capability of protecting from damage coloring substances which are sensitive to UV-A radiation and which are customarily present in cosmetics.

The cosmetic compositions provided in accordance with the present invention comprise a cosmetically acceptable carrier and, as the UV-A filter, an effective amount of one or more of the benzoxazole derivatives aforesaid. The cosmetic compositions in accordance with the present invention preferably contain at least one cosmetically acceptable salt of the compounds of formula I, the triethanolamine salt being particularly preferred. The amount of the compounds of formula I present in the cosmetic compositions provided in accordance with the present invention can vary within wide limits depending on the type of preparation contemplated. Such compositions preferably contain from about 0.01 to about 10 weight percent of one or more of the compounds of formula I based on the finished cosmetic preparation.

For example, creams and sun milks for the protection of the skin against UV-A radiation, i.e. light-screening preparations, would contain one or more of the compounds of formula I or their salts in a concentration of about 0.5 to about 10 percent by weight, perferably from about 2 to about 4 percent by weight. Such preparations would preferably also contain a UV-B filtering agent, i.e. a substance capable of absorbing radiation in the erythemal range.

In order to protect coloring substances present in cosmetic compositions from UV-A radiation, such compositions, e.g., shampoos or lotions, preferably contain one or more of the compounds of formula I or their salts, preferably a triethanolamine salt, added to such agents in a concentration of from about 0.01 to about 0.5 percent by weight. The compounds of formula I and their salts can also be incorporated in the same preferred concentrations to hair-care compositions, such as, for example, hair lotions, their treatments, hair toning reinforcers, and hair coloring agents, since the hair also suffers under the influence of UV-A radiation.

The above described cosmetic compositions can also contain other UV-A filters as well as UV-B filters.

The cosmetic compositions provided in accordance with the present invention are prepared by formulating one or more compounds of formula I or their cosmetically acceptable salts by conventional techniques customary in the cosmetic art with active substances, adjuvant substances, and carrier materials conventionally utilized in the appropriate cosmetic preparation. The resulting preparations are utilized in the same manner as similar preparations which do not contain the active compounds of formula I.

The following Examples illustrate the process provided by the present invention. Unless otherwise indicated, all temperatures are in degrees Centigrade:

EXAMPLE 1

Equimolar amounts of p-dimethylamino-benzoic acid and 2-aminophenol-4-sulfonic acid were added to a flask provided with a stirrer. Polyphosphoric acid was then added until a stirrable paste was obtained. The mixture was heated to 160° with stirring and maintained for 1 hour. The resulting dark brown liquid was allowed to cool to 100° and poured with stirring into a large amount of cold water. The product which separated was filtered, washed thoroughly with water, and resuspended in water. Dilute sodium hydroxide was added to the suspension until an almost clear solution was obtained (pH 7–7.5). The solution was filtered and subsequently acidified by pH 3–3.5. The 2-(p-dimethylaminophenyl)-benzoxazole-5-sulfonic acid which separated out was filtered, washed with water, and dried in a warming cabinet under a vacuum; melting point above 300°.

EXAMPLE 2

17.5 g of p-dimethylamino-benzoic acid and 22.0 g of 2-aminophenol-4-sulfonic acid were added to a flask provided with a stirrer. Polyphosphoric acid was then added until a stirrable paste was obtained. The mixture was heated to 160° with stirring and maintained for 1 hour. The resulting dark brown liquid was cooled to 100° and poured with stirring into a large amount of ice-cold water. The product which separated was filtered, washed thoroughly with water, and resuspended in water. Dilute ammonia solution was added to the suspension until an almost clear solution was obtained (pH 7–7.5). The dark brown solution was filtered and subsequently acidified to pH 3–3.5. The 2-(p-dimethylaminophenyl)-benzoxazole-5-sulfonic acid which separated was filtered, washed with water, and dried in a warming cabinet under a vacuum; melting point 338° (with decomposition).

Analysis: $C_{15}H_{14}N_2O_4S$ (318.35), Calculated: C 56.59; H 4.43; N 8.80; S 10.07%, Found: C 56.66; H 4.53; N 8.79; S 9.96% ($H_2O$-free).

EXAMPLE 3

2-(p-Dimethylaminophenyl)-benzoxazole-5-sulfonic acid was also obtained by reacting 10.0 g of p-dimethylamino-benzonitrile with 13.0 g of 2-aminophenol-4-sulfonic acid in accordance with the procedure of Example 1.

EXAMPLE 4

In accordance with the procedure of Example 1, 8.0 g of p-methylamino-benzoic acid were reacted with 10.0 g of 2-aminophenol-4-sulfonic acid to yield 2-(p-methylaminophenyl)-benzoxazole-5-sulfonic acid, melting point 333° (with decomposition).

Analysis: $C_{14}H_{12}N_2O_4S$ (304.32), Calculated: C 55.26; H 3.97; N 9.21; S 10.53%, Found: C 54.90; H 4.10; N 9.14; S 10.74% ($H_2O$-free).

EXAMPLE 5

11.0 g of p-diethylamino-benzoic acid and 10.5 g of 2-aminophenyl-4-sulfonic acid were reacted in accordance with the procedure of Example 1. After the reaction, the dark brown liquid was poured into water and the pH of the solution adjusted to pH 8 with sodium hydroxide. The resulting basic solution was filtered and saturated with sodium chloride until a dark brown mass was obtained. This mass was separated from the water, again dissolved in water, and the solution obtained saturated with sodium chloride. There are thus obtained the sodium salt of 2-(p-diethylamino-phenyl)-benzoxazole-5-sulfonic acid in the form of a powder which can be crystallized from alcohol/water, melting point 318°.

Analysis: $C_{17}H_{17}N_2O_4SNa$ (368.38) Calculated: C 55.43; H 4.65; N 7.60; S 8.70% Found: C 55.47; H 4.86; N 7.69; S 8.40% ($H_2O$-free).

EXAMPLE 6

In accordance with the procedure of Example 1, 5.0 g of ethyl 4-piperidinobenzoate were reacted with 4.2 g of 2-aminophenyl-4-sulfonic acid to yield 2-(p-piperidinophenyl)-benzoxazole-5-sulfonic acid, melting point 351° (with decomposition).

Analysis: $C_{18}H_{18}N_2O_4S$ (358.41), Calculated: C 60.32; H 5.06; N 7.82; S 8.95%, Found: C 60.32; H 5.09; N 7.88; S 8.90% ($H_2O$-free).

EXAMPLE 7

In accordance with the procedure of Example 1, 10.0 g of ethyl 4-pyrrolidinobenzoate were reacted with 8.7 g of 2-aminophenol-4-sulfonic acid to yield 2-(p-pyrrolidinophenyl)-benzoxazole-5-sulfonic acid, melting point 310° (with decomposition).

Analysis: $C_{17}H_{16}N_2O_4S$ (344.39), Calculated: C 59.29; H 4.68; N 8.13; S 9.31%, Found: C 60.28; H 4.76; N 8.16; S 9.00% ($H_2O$-free).

EXAMPLE 8

10.0 g of 2-(p-aminophenyl)-benzoxazole-5-sulfonic acid obtained in accordance with the procedure of Example 1 was suspended in 40 g of liquid ethylene oxide. The reaction vessel was heated to 100° under pressure for 4 hours. After cooling, the excess ethylene oxide was removed and the dark brown viscous mass dissolved in rectified alcohol. The resulting solution was treated with active carbon. The mixture was filtered, the solvent removed by evaporation, and the resulting residue dried under a vacuum. There was thus obtained a dark red honey-like mass: UV-spectrum $\lambda_{FSP}^{max} = 347$ nm.

The product comprises a mixture of compounds represented by the formula

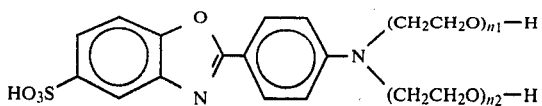

wherein $n_1$ and $n_2$ are independently integers of 1 to 10.

EXAMPLE 9

11.2 g of 2-(p-dimethylaminophenyl)-benzoxazole were dissolved in 26 ml of concentrated sulfuric acid. 16 ml of fuming sulfuric acid (oleum 60%) were then added thereto and the mixture heated to 200° for 1 hour. After cooling, the solution was poured into 1200 ml of acetone. The 2-(p-dimethylaminophenyl)-benzoxazole-6-sulfonic acid which separated was worked up in accordance with the procedure of Example 1; melting point 315° (with decomposition).

Analysis: $C_{15}H_{14}N_2O_4S$ (318.35),
Calculated: C 56.59; H 4.43; N 8.80; S 10.07%,
Found: C 56.20; H 4.33; N 8.85; S 10.19% ($H_2O$-free).

EXAMPLE 10

The procedure of Example 9 was repeated using 2-(p-dimethylaminophenyl)-5-methyl-benzoxazole to yield 2-(p-dimethylaminophenyl)-5-methyl-benzoxazole-6-sulfonic acid, melting point 302.6° (with decomposition).

Analysis: $C_{16}H_{16}N_2O_4S$ (332.37),
Calculated: C 57.82; H 4.85; N 8.43; S 9.65%,
Found: C 57.33; H 4.83; N 8.70; S 9.65% ($H_2O$-free).

EXAMPLE 11

The procedure of Example 9 was repeated using 2-(p-dimethylaminophenyl)-6-methyl-benzoxazole to yield 2-(p-dimethylaminophenyl)-6-methyl-benzoxazole-5-sulfonic acid, melting point 290° (with decomposition).

Analysis: $C_{16}H_{16}N_2O_4S$ (332.37),
Calculated: C 57.82; H 4.85; N 8.43; S 9.65%,
Found: C 58.20; H 4.95; N 8.57; S 9.42% ($H_2O$-free).

EXAMPLE 12

A sun-screen oil/water emulsion was prepared by conventional procedures from the following formulation:
- 5.00 g Ethylhexyl paramethoxy-cinnamic acid ester: Parsol MCX—Givaudan S.A.
- 3.00 g Diethanolamine cetyl phosphate: Amphisol—Givaudan S.A.
- 2.00 g Stearyl alcohol,
- 5.00 g Ester of a branched fatty acid of medium chain length with fatty alcohol,
- $C_{16}$-$C_{18}$: Cetiol SN—Henkel+Cie GmbH,
- 4.00 g Paraffin oil—low viscosity,
- 2.00 g Butyl stearate
- 0.10 g Propyl p-hydroxybenzoate.
- 0.40 g Carboxyvinyl polymer: Carbopol 940—Goodrich Chemical Co.
- 5.00 g 2-(p-Dimethylaminophenyl)-benzoxazole-5-sulfuric acid,
- 0.63 g Triethanolamine,
- 0.70 g of Sodium hydroxide,
- 2.00 g Propylene glycol,
- 0.20 g Methyl p-hydroxybenzoate,
- 0.20 g Imidazolidinyl-urea compound: Germall 115—Sutton Laboratories,
- 0.50 g D-Panthenol ethyl ether
- 0.50 g D-Panthenol
- 0.50 g Perfume and,
- 100 g Demineralized water.

EXAMPLE 13

A partial-fat oil/water sun-screen emulsion cream was prepared by conventional procedures from the following formulation:
- 5.000 g Ethylhexyl paramethoxy-cinnamic acid ester: Parsol MCX—Givaudan S.A.
- 5.600 g Lower oxyethylated saturated fatty alcohol: Cremophor A Solid—BASF AG
- 5.000 g Hard fat component of exclusively saturated vegetable fatty acids of
- chain length $C_{10}$-$C_{18}$: Softisan 100—Th. Goldschmidt AG
- 4.000 g Cetyl alcohol
- 4.000 g Stearyl alcohol
- 10.000 g Sesame oil
- 0.004 g Butyl hydroxy-anisole
- 0.016 g Butyl hydroxy-toluene
- 3.000 g 2-(p-Dimethylaminophenyl)-benzoxazole-5-sulfonic acid
- 0.360 g Sodium hydroxide.
- 0.200 g N-(3-chloroallyl)-hexaminium hydrochloride: Dowicil 200—Dow Chemical Co.
- 0.400 g Perfume and,
- 100 g Demineralized water.

EXAMPLE 14

A sun-screen oil/water emulsion lotion was prepared by conventional procedures from the following formulation:
- 5.00 g Ethylhexyl paramethoxy-cinnamic acid ester: Parsol MCX—Givaudan S.A.
- 5.00 g Polyoxyethylene-glycerine monostearate: Tagat S—Th. Goldschmidt AG
- 2.00 g Glycerine monostearate
- 10.00 g Isopropyl myristate: Deltyl Extra—Givaudan S.A.
- 8.00 g Paraffin oil-low viscosity
- 2.00 g Petroleum jelly, white
- 2.00 g Mixed alkyl-branched fatty acid ester: PCL Liquid—Dragoco AG
- 3.00 g Stearyl alcohol
- 2.00 g Triglyceride mixture of saturated vegetable fatty acids of medium chain
- length and with a proportion of an essential fatty acid: Migliol 818—Dynamit Nobel AG
- 3.00 g 2-(p-Dimethylaminophenyl)-benzoxazole-5-sulfonic acid
- 1.46 g Triethanolamine
- 1.00 g Glycerine
- 0.20 g N-(3-chloroally)-hexaminium hydrochloride: Dowicil 200—Dow Chemical Co.
- 0.40 g Perfume and,
- 100 g Demineralized water.

EXAMPLE 15

A sun-screen oil/water emulsion cream was prepared by conventional procedures from the following formulation:

- 15.0 g Colloid dispersed mixture of 90 parts of cetyl-stearyl alcohol and 10 parts of
- sodium cetylstearyl sulfate: Lanette N—Henkel+Cie GmbH
- 5.0 g Ethylhexyl paramethoxy-cinnamic acid ester: Parsol MCX—Givaudan S.A.
- 5.0 g Oleic acid decyl ester: Cetiol V—Henkel+Cie GmbH
- 5.0 g Petroleum jelly, white
- 0.1 g Propyl p-hydroxy-benzoate
- 1.0 g Isopropyl myristate: Deltyl Extra—Givaudan S.A.
- 2.0 g Mixed alkyl-branched fatty acid ester: PCL Liquid—Dragoco AG
- 5.0 g 2-(p-Dimethylaminophenyl)-benzoxazole-5-sulfonic acid
- 0.6 g Sodium hydroxide
- 4.0 g Propylene glycol
- 0.2 g Methyl p-hydroxybenzoate
- 0.2 g Imidazolidinyl-urea compound: Germall 115—Sutton Laboratories
- 0.5 g Perfume, and
- 100 g Demineralized water.

EXAMPLE 16

A sun-screen gel was prepared by conventional procedures from the following formulation:

- 5.0 g Ethylhexyl paramethoxy-cinnamic acid ester: Parsol MCX-Givaudan S.A.
- 13.0 g Cetylstearyl alcohol with about 30 mol of ethylene oxide: Eumulgin B 3—Henkel+Cie GmbH
- 20.0 g Polyol-fatty acid ester: Cetiol HE—Henkel+Cie GmbH
- 0.5 g Mixture of p-hydroxybenzoic acid esters in 2-phenoxy-ethyl alcohol: Phenonip—Nipa Laboratories
- 2.0 g Isopropyl myristate: Deltyl Extra—Givaudan S.A.
- 5.0 g 2-(p-Dimethylaminophenyl)-benzoxazole-5-sulfonic acid
- 3.1 g Triethanolamine
- 5.0 g Propylene glycol
- 0.5 g Perfume, and,
- 100 g Demineralized water.

EXAMPLE 17

A non-aerosol hair spray was prepared by conventional procedures from the following formulation:

| | |
|---|---|
| 10.0 g | Poly(methyl vinyl ether/maleic acid monoalkyl ester): Gantrez ES 425-GAF Corp. |
| 0.1 g | Diisopropyl adipate |
| 0.1 g | Polyphenylmethyl-siloxane: Dow Corning 556 Fluid-Dow Corning Corp. |
| 84.0 g | Rectified alcohol |
| 0.2 g | Perfume |
| 1.2 g | Ammonium hydroxide 25% |
| 0.1 g | Alkyltrimethylammonium chloride-(alkyl = predominantly $C_{20}$-$C_{22}$): Genamin KDM-Hoechst AG |
| 0.5 g | 2-(p-Dimethylaminophenyl)-benzoxazole-5-sulfonic acid |
| 3.8 g | Demineralized water |
| 100.00 g | |

EXAMPLE 18

A hair lotion, designated lotion A (control), was prepared by conventional procedures from the following formulation:

- 45.00 g Rectified alcohol
- 0.10 g Perfume
- 0.25 g D-Panthenol ethyl ether
- 0.25 g D-Panthenol
- 0.05 g Cetylpyridinium chloride
- 0.60 mg F D & C Blue No. 1 Col. Ind. No. 42090 (Triphenylmethane coloring substance), and,
- 100 g Demineralized water. To 100 g samples of this formulation were added 0.025 g of 2-(p-dimethylaminophenyl)-benzoxazole-5-sulfonic acid and 0.013 g of triethanolamine (lotion B) and 0.050 g of 2-(p-dimethylaminophenyl)-benzoxazole-5-sulfonic acid and 0.026 g of triethanolamine (lotion C), respectively.

Light test (Xenotest)

Samples of the foregoing hair lotions A, B, and C were subjected to a Xenotest. In this test 3 hours and 6 hours exposure corresponded to about 3 months and 6 months exposure, respectively, to artificial light (1000 Lux) for 10–12 hours per day. The appearance of each lotion after the exposure was compared with that of a sample of the corresponding lotion which had not been subjected to the test conditions. The results are given in Table I.

TABLE I

| Hair Lotion | Appearance after 3 hours exposure | Appearance after 6 hours exposure |
|---|---|---|
| A | Distinct color change to green, lighter | Strong color change to turquoise |
| B | Unaltered | No color change, but a trace lighter |
| C | Unaltered | No color change, but a trace lighter |

EXAMPLE 19

A hair lotion designated lotion D (control), was prepared by conventional procedures from the following formulation:

- 45.0 g Rectified alcohol
- 0.1 g Perfume
- 0.5 g Isoadipate (diisopropyl adipate)
- 0.8 mg F D & C Yellow No. 6 Col. Ind. No. 15985 (Monoazo coloring substance) and,
- 100 g Demineralized water.

To 100 g samples of this formulation were added 0.025 g of 2-(p-dimethylaminophenyl)-benzoxazole-5-sulfonic acid and 0.013 g of triethanolamine (lotion E) and 0.050 g of 2-(p-dimethylaminophenyl)-benzoxazole-5-sulfuric acid and 0.026 g of triethanolamine (lotion F), respectively.

Hair lotions D, E, and F were subject to a Xenotest in accordance with the procedure of Example 18 for 3, 6, 12, and 27 hours exposure. The results are given in Table II.

TABLE II

| Hair lotion | Appearance after 3 hours exposure | Appearance after 6 hours expsoure |
|---|---|---|
| D | Unaltered | Slight color change, more yellow and less orange |
| E | Unaltered | Unaltered |
| F | Unaltered | Unaltered |

| Hair lotion | Appearance after 12 hours exposure | Appearance after 27 hours exposure |
|---|---|---|
| D | Slight color change, more yellow and less orange | More Yellow and less orange |
| E | Unaltered | Unaltered |
| F | Unaltered | Unaltered |

EXAMPLE 20

A golden-blonde designated preparation A (control) was prepared by conventional procedures from the following formulation:

45.000 g Rectified alcohol,
5.000 g Vinyl acetate mixed polymer: Aristoflex A 60%—Hoechst AG,
0.200 g Acetyltriethylcitrate: Citroflex A-2—Pfizer AG,
49.350 g Demineralized water,
0.320 g Ammonium hydroxide 25%
0.100 g Perfume,
0.015 g F D & C Yellow No. 6 Col. Ind. No. 15985, (Monoazo coloring substance),
0.015 g F D & C Yellow No. 5 Col. Ind. No. 19140 (Pyrazolone coloring substance).

To additional samples of this preparation were added 0.025 g of 2-(p-dimethylaminophenyl)-benzoxazole-5-sulfonic acid (preparation B) and 0.050 g of 2-(p-dimethylaminophenyl)-benzoxazole-5-sulfonic acid (preparation C), respectively.

Preparations A, B, and C were subjected to a Xenotest in accordance with the procedure of Example 18 for 12, 24, and 48 hours exposure. The results are given in Table III.

TABLE III

| Hair toning reinforcer Golden-blonde Preparation | Appearance after 12 hours exposure | Appearance after 24 hours exposure | Appearance after 48 hours exposure |
|---|---|---|---|
| A | Unaltered | Unaltered | A trace lighter and less orange |
| B | Unaltered | Unaltered | Unaltered |
| C | Unaltered | Unaltered | Unaltered |

EXAMPLE 21

A clear shampoo, designated shampoo A (control), was prepared by conventional procedures from the following formulation:

25.0 g Fatty acid amidopropyl-dimethylaminoacetic acid-betaine: Tego-Betaine L 7—Th. Goldschmidt AG
20.0 g Triethanolamine lauryl ether sulfate: Texapon NT—Henkel+Cie GmbH
3.0 g Coconut oil diethanolamide: Comperlan KD—Henkel+Cie GmbH
0.5 g D-Panthenol ethyl ether
0.2 g N-(3-chloroallyl)-hexaminium hydrochloride: Dowicil 200—Dow Chemical Co.
1.5 mg F D & C blue No. 1 Col. Ind. No. 42090 (Triphenylmethane coloring substance)
100 g Demineralized water.

To 100 g samples of the above clear shampoo were added 0.050 g of 2-(p-dimethylaminophenyl)-benzoxazole-5-sulfonic acid and 0.026 g of triethanolamine (shampoo B) and 0.050 g of 2-hydroxy-4-methoxy-benzophenone-5-sulfonic acid: Uvinul MS 40—GAF Corp. (shampoo C), respectively.

An attempt was made to prepare shampoo A with 0.050 g of 2,2',4,4'-tetrahydroxy-benzophenone: Uvinul D 50—GAF Corp. However, this substance could not be brought into solution after 1 hour of stirring at 50°. This preparation was not tested.

Clear blue shampoos A, B, and C were subjected to a Xenotest in accordance with the procedure of Example 18 and under the same conditions. The results are given in Table IV.

TABLE IV

| Clear shampoo | Appearance after 3 hours exposure | Appearance after 6 hours exposure |
|---|---|---|
| A | Pink | Pink |
| B | Blue, but a trace lighter | Light blue |
| C | Almost colorless | Pink |

I claim:

1. Compounds represented by the formula

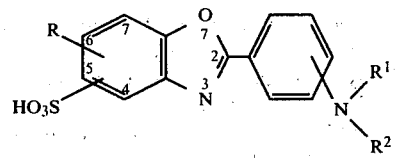

wherein R is in the 5- or 6-position and is hydrogen or an alkyl group containing 1 to 4 carbon atoms and $R^1$ and $R^2$ are independently hydrogen, an alkyl group containing 1 to 4 carbon atoms or a group having the formula $—(XO)_n—H$, wherein X is ethylene or ethylene substituted by methyl or ethyl and which contains a total of 2 to 4 carbon atoms and n is an integer of 1 to 10, at least one of $R^1$ and $R^2$ being other than hydrogen, or $R^1$ and $R^2$, taken together with the nitrogen to which they are attached, form a 5- to 7-membered, saturated heterocyclic ring, and cosmetically acceptable salts thereof.

2. Compounds in accordance with claim 1 wherein R is hydrogen and n is 1.

3. Compounds in accordance with claim 1 wherein $R^1$ and $R^2$ are methyl.

4. Compounds in accordance with claim 1 wherein the group $HO_3S—$ is in the 5-position.

5. Compounds in accordance with claim 1 wherein the group $—NR^1R^2$ is in the para position.

6. A compound in accordance with claim 1 wherein said compound is 2-(p-dimethylaminophenyl)-benzoxazole-5-sulfonic acid or a cosmetically acceptable salt thereof.

7. A compound in accordance with claim 1 selected from the group consisting of:
2-(p-methylaminophenyl)-benzoxazole-5-sulfonic acid;
2-(p-diethylaminophenyl)-benzoxazole-5-sulfonic acid sodium salt;
2-(piperidinophenyl)-benzoxazole-5-sulfonic acid;

2-(p-pyrrolidinophenyl)-benzoxazole-5-sulfonic acid;
2-(p-dimethylaminophenyl)-benzoxazole-6-sulfuric acid;
2-(p-dimethylaminophenyl)-5-methyl-benzoxazole-6-sulfonic acid; and
2-(p-dimethylaminophenyl)-6-methyl-benzoxazole-5-sulfonic acid.
8. Compounds in accordance with claim 1 represented by the formula
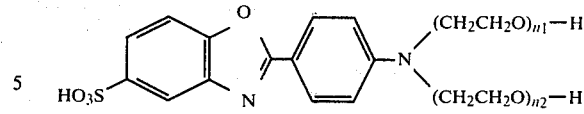
wherein $n_1$ and $n_2$ are independently integers from 1 to 10.
* * * * *